US010196758B2

(12) United States Patent
Kraft et al.

(10) Patent No.: US 10,196,758 B2
(45) Date of Patent: Feb. 5, 2019

(54) POLYSACCHARIDE FIBERS AND METHOD FOR PRODUCING SAME

(71) Applicant: LENZING AG, Lenzing (AT)

(72) Inventors: Gregor Kraft, Timelkam (AT); Gert Kroner, Seewalchen (AT); Thomas Röder, Vöcklabruck (AT); Heinrich Firgo, Vöcklabruck (AT)

(73) Assignee: LENZING AKTIENGESELLSCHAFT, Lenzing (AT)

(*) Notice: Subject to any disclaimer, the term of this patent is extended or adjusted under 35 U.S.C. 154(b) by 32 days.

(21) Appl. No.: 14/899,225

(22) PCT Filed: Jun. 13, 2014

(86) PCT No.: PCT/AT2014/000122
§ 371 (c)(1),
(2) Date: Dec. 17, 2015

(87) PCT Pub. No.: WO2014/201481
PCT Pub. Date: Dec. 24, 2014

(65) Prior Publication Data
US 2016/0177471 A1  Jun. 23, 2016

(30) Foreign Application Priority Data
Jun. 18, 2013  (AT) .................. A 490/2013

(51) Int. Cl.
*D01D 5/06* (2006.01)
*D01F 2/02* (2006.01)
*D01F 2/24* (2006.01)
*C08B 37/00* (2006.01)
*A61L 15/28* (2006.01)
*B29C 47/00* (2006.01)
*D01F 9/00* (2006.01)
*D04H 1/4258* (2012.01)
*D04H 3/013* (2012.01)
*B29L 31/00* (2006.01)

(52) U.S. Cl.
CPC .............. *D01D 5/06* (2013.01); *A61L 15/28* (2013.01); *B29C 47/0004* (2013.01); *B29C 47/0014* (2013.01); *B29C 47/0088* (2013.01); *C08B 37/0009* (2013.01); *D01F 2/02* (2013.01); *D01F 2/24* (2013.01); *D01F 9/00* (2013.01); *D04H 1/4258* (2013.01); *D04H 3/013* (2013.01); *B29K 2005/00* (2013.01); *B29L 2031/731* (2013.01)

(58) Field of Classification Search
CPC .......... D21H 13/02; D21H 13/08; D01F 2/02; D01F 2/06; D01F 2/08; D01F 2/24; C08L 1/02; C08L 1/24; C08L 5/02; C08B 37/0009; C08B 37/0021; D01D 5/06
USPC ....... 162/157.7; 264/188, 189, 178 F, 178 R, 264/205, 207; 536/123.1, 123.12
See application file for complete search history.

(56) References Cited

U.S. PATENT DOCUMENTS

| 2,179,181 | A | 11/1939 | Graenacher et al. |
| 2,914,414 | A | 11/1959 | Novak et al. |
| 3,447,939 | A | 6/1969 | Johnson |
| 3,600,379 | A | * 8/1971 | Nizovsky .................. D01F 2/08 106/166.01 |
| 3,844,287 | A | 10/1974 | Smith |
| 4,129,679 | A | 12/1978 | Woodings |
| 4,289,824 | A | 9/1981 | Smith |
| 4,306,059 | A | 12/1981 | Yokobayashi et al. |
| 4,562,020 | A | 12/1985 | Hijiya et al. |
| 5,403,530 | A | 4/1995 | Taylor |
| 5,589,125 | A | 12/1996 | Zikeli et al. |
| 5,725,821 | A | 3/1998 | Gannon et al. |
| 5,795,522 | A | 8/1998 | Firgo et al. |
| 6,042,769 | A | 3/2000 | Gannon et al. |
| 6,113,842 | A | 9/2000 | Weigel et al. |
| 6,284,479 | B1 | 9/2001 | Nichols |
| 6,821,591 | B2 | 11/2004 | Gard et al. |
| 7,000,000 | B1 | 2/2006 | O'Brien |
| 9,175,423 | B2 | 11/2015 | O'Brien et al. |
| 9,701,800 | B2 | 7/2017 | Durnberger et al. |
| 10,030,323 | B2 | 7/2018 | Durnberger et al. |
| 2002/0022100 | A1 | 2/2002 | Gard et al. |
| 2002/0167110 | A1 | 11/2002 | Schlossnikl et al. |
| 2003/0185863 | A1 | 10/2003 | Bengs et al. |
| 2009/0165969 | A1 | 7/2009 | Luo |
| 2011/0200776 | A1 | 8/2011 | Zikeli et al. |
| 2013/0087938 | A1 | 4/2013 | O'Brien et al. |
| 2013/0161562 | A1* | 6/2013 | O'Brien .................... C09K 3/00 252/363.5 |
| 2013/0161861 | A1* | 6/2013 | O'Brien .................... D01D 5/06 264/183 |
| 2013/0244288 | A1 | 9/2013 | O'Brien et al. |
| 2013/0313737 | A1 | 11/2013 | O'Brien |
| 2014/0367896 | A1 | 12/2014 | Zikeli et al. |
| 2016/0053061 | A1 | 2/2016 | Durnberger et al. |
| 2016/0053406 | A1 | 2/2016 | Durnberger et al. |
| 2016/0060792 | A1 | 3/2016 | Durnberger et al. |
| 2016/0138195 | A1 | 5/2016 | Kraft et al. |
| 2016/0138196 | A1 | 5/2016 | Roder et al. |
| 2016/0144065 | A1 | 5/2016 | Roder et al. |
| 2016/0177471 | A1 | 6/2016 | Kraft et al. |
| 2017/0283568 | A1 | 10/2017 | Durnberger et al. |

FOREIGN PATENT DOCUMENTS

AT     287905 B     2/1971
AT     402828 B     9/1997
(Continued)

OTHER PUBLICATIONS

Singha, K., "Importance of the Phase Diagram in Lyocell Fiber Spinning", International Journal of Materials Engineering, (2012) pp. 10-16.

(Continued)

Primary Examiner — Eric Hug
(74) Attorney, Agent, or Firm — Venable LLP

(57) ABSTRACT

The present invention relates to a direct dissolving process for the production of polysaccharide fibers which contain α(1→3)-glucan as a fiber-forming substance, with aqueous sodium hydroxide solution as a solvent, as well as to the fibers made thereby, and to their use.

7 Claims, No Drawings

(56) References Cited

FOREIGN PATENT DOCUMENTS

| | | | |
|---|---|---|---|
| DE | 2550345 | A1 | 5/1977 |
| DE | 3036415 | A1 | 4/1981 |
| DE | 19544097 | C1 | 7/1997 |
| DE | 10029044 | A1 | 1/2002 |
| DE | 10035798 | A1 | 1/2002 |
| DE | 10261496 | A1 | 7/2004 |
| EP | 0049710 | A1 | 4/1982 |
| EP | 0 158 884 | A2 | 10/1985 |
| EP | 0 328 317 | A1 | 8/1989 |
| EP | 0 356 419 | B1 | 12/1992 |
| EP | 0 584 318 | B1 | 3/1994 |
| GB | 2062652 | A | 5/1981 |
| JP | 0351366 | H | 3/1991 |
| JP | 2006-211989 | A | 8/2006 |
| WO | 89/01062 | A1 | 2/1989 |
| WO | 95/35340 | A1 | 12/1995 |
| WO | 97/04148 | A1 | 2/1997 |
| WO | 97/07266 | A1 | 2/1997 |
| WO | 98/42492 | A2 | 10/1998 |
| WO | 98/55673 | A1 | 12/1998 |
| WO | 00/23250 | A1 | 4/2000 |
| WO | 00/43580 | A1 | 7/2000 |
| WO | 2012/073019 | A1 | 6/2012 |
| WO | 2013/006876 | A1 | 1/2013 |
| WO | 2013020919 | A1 | 2/2013 |
| WO | 2013/036918 | A1 | 3/2013 |
| WO | 2013/036968 | A1 | 3/2013 |
| WO | 2013030400 | A1 | 3/2013 |
| WO | 2013/052730 | A1 | 4/2013 |
| WO | 2014/099724 | A1 | 6/2014 |
| WO | 2014/165881 | A | 10/2014 |

OTHER PUBLICATIONS

Schmidt, M., Lenzinger Berichte 9 (1994) pp. 95-97.
Ogawa, K., et al., "Crystal Structure of (1,3)-Alpha-D-Glucan", Water Soluble Polymers: Synthesis Solution Properties and Applications, American Chemical Society, vol. 141, (1980) p. 354.
Helfried Stover, "Zur Fasernassscheverung von Viskosefasern" Faserforschung und Textiltechnik 19, issue 10, (1968) pp. 447-452.
Rosenau et al., "The Chemistry of side reactions and byproduct formation in the system NMMO/cellulose (Lyocell process," Prog. Polym. Sci., vol. 26, pp. 1763-1837 (2001).
Akira Misaki, Elsinan, an Extracellular alpha 1,3:1,4 Glucan Produced by Elsinoe Ieucospila: Production, Structure, Properties and Potential Food Utilization, Foods Food Ingredients J. Jpn, vol. 209, No. 4, Jan. 1, 2004, available at: http://www.ffcr.or.jp/zaidan/ffcrhome.nsf/7bd44c20b0dc562649256502001b65e9/a574be4bca4c288149256e82000f39bb/$FILE/209(4)3.pdf.
Zhang, P. et al., Effects of urea and sodium hydroxide on the molecular weight and conformation of alpha-(1>3)-d-glucan from Lentinus edodes in aqueous solution, Carbohydrate Research, Pergamon, GB, Carbohydrate Research, Pergamon, GB, vol. 327 No. 4 pp. 431-438, Aug. 7, 2000.
Simpson, et al., *Streptococcus salivarius*, Microbiology, vol. 41 pp. 1451-1460 (1995).
International Search Report for PCT/AT2014/000122 dated Oct. 3, 2014.
International Search Report for PCT/AT2014/000124 dated Oct. 2, 2014.
International Search Report for PCT/AT2014/000125 dated Sep. 26, 2014.
International Search Report for PCT/AT2014/000123 dated Sep. 26, 2014.
International Preliminary Report in Patentability and Written Opinion of the International Searching Authority issued in International Application No. PCT/AT2014/00122 (10 pages).
International Preliminary Report in Patentability and Written Opinion of the International Searching Authority issued in International Application No. PCT/AT2014/00123 (8 pages).
International Preliminary Report in Patentability and Written Opinion of the International Searching Authority issued in International Application No. PCT/AT2014/00124 (8 pages).
International Preliminary Report in Patentability and Written Opinion of the International Searching Authority issued in International Application No. PCT/AT2014/00125 (8 pages).
U.S. Appl. No. 16/007,641, filed Jun. 13, 2018.
U.S. Appl. No. 15/980,140, filed May 15, 2018.
U.S. Appl. No. 15/988,401, filed May 24, 2018.
U.S. Appl. No. 16/038,471, filed Jul. 18, 2018.
U.S. Appl. No. 15/932,303, filed Feb. 16, 2018.

* cited by examiner

POLYSACCHARIDE FIBERS AND METHOD FOR PRODUCING SAME

FIELD OF THE INVENTION

The present invention relates to a direct dissolving process for the production of polysaccharide fibers which contain α(1→3)-glucan as a fiber-forming substance, with aqueous sodium hydroxide solution as a solvent, as well as to the fibers made thereby, and to their use.

BACKGROUND OF THE INVENTION

Polysaccharides are becoming increasingly important, as they are materials that can be obtained from renewable raw materials. One of the most frequently occurring polysaccharides is cellulose. Cotton fibers, which consist almost exclusively of cellulose, are an example of the significance of polysaccharides. However, also materials obtained from other cellulosic raw materials, e.g., cellulosic synthetic fibers, are continuing to gain in importance.

The generic names "viscose fibers" and "modal fibers" were assigned by BISFA (the International Bureau for the Standardization of Man-made Fibers) to cellulose fibers produced through chemical derivatization of cellullose with the help of aqueous sodium hydroxide solution and carbon disulfide ($CS_2$).

The name "modal fiber" is a generic term which, as defined by BISFA, stands for a cellulose fiber having a defined high wet strength and an equally defined high wet modulus (i.e., the force required to produce an elongation of the fiber of 5% in its wet state).

However, to date, only one method for the large-scale production of fibers of the viscose and modal types has gained acceptance, namely, the viscose process and variations thereof.

From many patent specifications and other publications, it has generally been known to those skilled in the art for quite some time how this method is carried out. A method for the production of modal fibers is, for example, known from AT 287.905 B.

The big downside of all viscose processes is the use of $CS_2$ that must be recovered with great effort.

The generic name "lyocell fibers" was assigned by BISFA to cellulose fibers produced from solutions in an organic solvent without the formation of a derivative.

However, to date, only one method for the large-scale production of fibers of the lyocell type has gained acceptance, namely, the amine-oxide process. In this method, a tertiary amine oxide, preferably N-methylmorpholine-N-oxide (NMMO), is used as the solvent.

Tertiary amine oxides have long been known as alternative solvents for cellulose. It is known from U.S. Pat. No. 2,179,181, for example, that tertiary amine oxides are capable of dissolving pulp without derivatization and that cellulosic molded bodies, e.g., fibers, can be made from these solutions. U.S. Pat. No. 3,447,939 describes cyclic amine oxides used as solvents for cellulose.

From numerous patent specifications and other publications, it has been known to those skilled in the art for quite some time how this method is carried out. EP 356 419 B1, for example, describes how the solution is prepared, and EP 584 318 B1 describes how such solutions of cellulose in aqueous tertiary amine oxides are spun.

Being a direct dissolving process, the lyocell process is significantly safer from an ecological perspective than the viscose processes, however, it comes with disadvantages in terms of process engineering, as, due to the economic necessity of providing nearly completely closed process cycles, substances may accumulate in the cycles.

U.S. Pat. No. 7,000,000 describes fibers obtained by spinning a solution of polysaccharides which substantially consist of repeating hexose units linked via α(1→3)-glycosidic bonds. These polysaccharides can be produced by bringing an aqueous solution of saccharose into contact with glucosyltransferase (GtfJ), isolated from *Streptococcus salivarius* (Simpson et al., Microbiology, vol. 41, pp 1451-1460 (1995)). As used in this context, "substantially" means that within the polysaccharide chains there may exist occasional defective locations where other bond configurations may occur. For the purposes of the present invention, these polysaccharides shall be referred to as "α(1→3)-glucan".

U.S. Pat. No. 7,000,000 first discloses possibilities for the enzymatic production of α(1→3)-glucan from monosaccharides. In this way, relatively short-chained polysaccharides can be produced without the loss of monomer units, as the polymer chains are built from the monomer units. Contrary to the production of short-chained cellulose molecules, the production of α(1→3)-glucan keeps getting less expensive the shorter the polymer chains are, as in that case the required residence time in the reactors will be short.

According to U.S. Pat. No. 7,000,000, the α(1→3)-glucan is to be derivatized, preferably acetylated. Preferably, the solvent is an organic acid, an organic halogen compound, a fluorinated alcohol, or a mixture of such components. These solvents are costly and complex to regenerate.

However, studies have also shown that α(1→3)-glucans dissolve in diluted aqueous sodium hydroxide solution.

Object

In view of such prior art, the object was therefore to provide an alternative direct dissolving process for the production of polysaccharide fibers, which makes do without the $CS_2$ needed in the viscose process and without the effort-consuming closure of cycles of a lyocell process.

DESCRIPTION OF THE INVENTION

The above described object is solved by a new direct dissolving process for the production of a polysaccharide fiber whose fiber-forming substance is α(1→3)-glucan, the direct dissolving process being based on aqueous sodium hydroxide solution.

Hence, the subject-matter of the present invention is, on the one hand, a method for the production of a polysaccharide fiber whose fiber-forming substance is α(1→3)-glucan, the method being a direct dissolving process and the solvent being aqueous sodium hydroxide solution.

Surprisingly, it was found that standard spin baths as used in the viscose process (they contain about 100 g/l $H_2SO_4$ and about 250 g/l $Na_2SO_4$) yield very poor results, but that two other, very different spin bath compositions yield significantly better results.

1. High-acid spinning: it was discovered that filament formation and the stretchability of the regenerated filament improve significantly when increasing the concentration of sulfuric acid in the spin bath. The examined range with good spinning characteristics reaches from 200 to 500 grams of sulfuric acid per liter of spin bath.

2. Low-acid spinning: the second spinning range, which exhibited a significantly better spinning reliability, is at very low acid concentrations below 60 grams per liter of spin bath, preferably from 20-60 g/l. Good results were also obtained using a two-bath system, where the first bath has very high salt contents and a very low acid concentration, whereby the spun filament is only coagulated at first and is regenerated only in the second, acid regeneration bath.

In a preferred embodiment of the inventive method, the $H_2SO_4$ concentration in the spin bath is therefore between 200 and 500 g/l.

In a second preferred embodiment of the inventive method, the $H_2SO_4$ concentration in the spin bath is therefore between 20 and 60 g/l.

In a preferred embodiment of the inventive method, the spun fiber is subsequently stretched in an acid regeneration bath.

According to the invention, the NaOH concentration in the spinning solution is to be between 4.0 and 5.5% by weight, related to the total quantity of the spinning solution. Outside this range, the solubility of the glucan is not sufficiently ensured.

For the purposes of the present invention, the term "fiber" shall comprise both staple fibers having a defined staple length and continuous filaments. All principles of the invention that are described hereinafter generally apply to both staple fibers and continuous filaments.

The single fiber titer of the inventive fibers can be between 0.1 and 10 dtex. Preferably, it is between 0.5 and 6.5 dtex, and more preferably between 0.9 and 6.0 dtex. In the case of staple fibers, the staple length is usually between 0.5 and 120 mm, preferably between 20 and 70 mm, and more preferably between 35 and 60 mm. In the case of continuous filaments, the number of individual filaments in the filament yarn is between 50 and 10,000, preferably between 50 and 3,000.

The $\alpha(1\rightarrow 3)$-glucan can be prepared by bringing an aqueous solution of saccharose into contact with glucosyltransferase (GtfJ) isolated from *Streptococcus salivarius* (Simpson et al., Microbiology, vol. 41, pp 1451-1460 (1995)).

In a preferred embodiment of the method according to the invention, at least 90% of the $\alpha(1\rightarrow 3)$-glucan are hexose units and at least 50% of the hexose units are linked via $\alpha(1\rightarrow 3)$-glycosidic bonds.

The method for the production of the inventive fiber consists of the following steps:

1. Preparing an $\alpha(1\rightarrow 3)$-glucan solution in diluted aqueous sodium hydroxide solution.
2. Extruding the $\alpha(1\rightarrow 3)$-glucan-containing spinning solution through a spinneret into a sulfuric acid spin bath, stretching the fibers in an acid regeneration bath, and post-treatment.

The concentration of the fiber-forming substance in the spinning solution can be between 4 and 18% by weight, preferably it is between 4.5 and 12% by weight.

The degree of polymerization of the $\alpha(1\rightarrow 3)$ glucan employed in the method according to the invention, expressed as weight average $DP_w$, can be between 200 and 2000; values between 500 and 1000 are preferred.

In a preferred embodiment at least 90% of the $\alpha(1\rightarrow 3)$-glucan of the polysaccharide fiber according to the invention are hexose units and at least 50% of the hexose units are linked via $\alpha(1\rightarrow 3)$-glycosidic bonds.

The above described polysaccharide fiber whose fiber-forming substance is $\alpha(1\rightarrow 3)$-glucan and which was produced using the also above described direct dissolving process in aqueous sodium hydroxide solution is also the subject-matter of the present invention.

The use of the inventive fibers for the production of textile products such as yarns, woven fabrics, or knitted fabrics as well as of various dry-laid and wet-laid papers, nonwovens, hygiene articles such as tampons, panty liners, and diapers, and of other nonwovens, especially absorbent nonwoven products, is also the subject-matter of the present invention.

The invention will be described below with reference to examples. However, the invention is not expressly limited to these examples but also includes all other embodiments that are based on the same inventive concept.

EXAMPLES

The degree of polymerization of the $\alpha(1\rightarrow 3)$-glucans was determined by means of GPC in DMAc/LiCl. Subsequently, it is always the weight average of the degree of polymerization ($DP_w$) that is specified.

Example 1

An aqueous glucan solution containing 9% of $\alpha(1\rightarrow 3)$-glucan with a $DP_w$ of 800 as well as 4.5% by weight of NaOH was cooled down to 3° C., filtered, and deaerated. By using a spinneret, the solution was extruded into a spin bath at 35° C., containing 300 g/l of sulfuric acid, and 50 g/l of sodium sulfate. The spinneret had 53 perforations with a diameter of 50 μm. In order to achieve adequate fiber strength, stretching in the regeneration bath (97° C., 25 g/l $H_2SO_4$) was carried out. The draw-off velocity was 30 m/min.

The properties of the obtained fibers are listed in Table 1.

Example 2

An aqueous glucan solution containing 9% of $\alpha(1\rightarrow 3)$-glucan with a $DP_w$ of 1000 as well as 4.8% by weight of NaOH was cooled down to 0° C., filtered, and deaerated. By using a spinneret, the solution was extruded into a spin bath at 20° C., containing 35 g/l of sulfuric acid, 280 g/l of sodium sulfate, and 45 g/l of zinc sulfate. The spinneret had 53 perforations with a diameter of 40 μm. In order to achieve adequate fiber strength, stretching in the regeneration bath (92° C., 55 g/l $H_2SO_4$) was carried out. The draw-off velocity was 25 m/min. The properties of the obtained fibers are listed in Table 1.

TABLE 1

| example | titer dtex | FFk cN/tex | FDk % |
|---------|------------|------------|-------|
| ex. 1   | 1.7        | 15.3       | 11.1  |
| ex. 2   | 1.7        | 19.1       | 9.2   |

FFk fiber strength, conditioned
FDk fiber elongation, conditioned

What is claimed is:

1. A method for the production of a polysaccharide fiber whose fiber-forming substance is $\alpha(1\rightarrow 3)$-glucan, wherein the method is a direct dissolving process which comprises the step of spinning the fiber by extruding a spinning solution comprising between 4.5% and 12% by weight of the fiber forming substance and an aqueous sodium hydroxide solution, wherein the spinning occurs in a spin bath comprising sulfuric acid, and wherein a spun fiber is formed.

2. The method according to claim 1, wherein the aqueous sodium hydroxide solution concentration in the spinning solution is between 4.0 and 5.5% by weight related to the total quantity of the spinning solution.

3. The method according to claim 1, wherein the spin bath comprises $H_2SO_4$ in a concentration between 200 and 500 g/l.

4. The method according to claim 1, wherein the spin bath comprises $H_2SO_4$ in a concentration between 20 and 60 g/l.

5. The method according to claim 1, wherein the spun fiber is subsequently stretched in an acid regeneration bath.

6. The method according to claim 1, wherein at least 90% of the $\alpha(1\rightarrow3)$-glucan are hexose units and at least 50% of the hexose units are linked via $\alpha(1\rightarrow3)$-glycosidic bonds.

7. The method according to claim 1, 2, 3, 4, 5, or 6, wherein the fiber is selected from the group consisting of a staple fiber and a continuous filament.

* * * * *